United States Defensive Publication [19] (H) [11] T998,006

Mee [43] Sep. 2, 1980

[54] NONDIFFUSIVE COMPOUNDS COMPRISED OF A SENSITIZING DYE MOIETY AND AN IMAGE DYE MOIETY JOINED BY A RADIATION CLEVABLE LINKAGE

[75] Inventor: John D. Mee, Rochester, N.Y.

[73] Assignee: Eastman Kodak Company, Rochester, N.Y.

[21] Appl. No.: 64,693

[22] Filed: Aug. 8, 1979

Related U.S. Application Data

[62] Division of Ser. No. 12,171, Feb. 14, 1979.

[51] Int. Cl.[3] ..... C07C 29/00; C07C 43/00; C07C 46/00

[52] U.S. Cl. ..... 260/156; 260/158; 260/159; 260/163; 260/199; 542/451

[57] ABSTRACT

Radiation-cleavable nondiffusible compounds for providing a transfer dye image are comprised of a spectral sensitizing dye moiety and a diffusible image dye moiety joined by a linkage in the spectral sensitizing dye moiety which is cleaved upon absorption of radiation by the spectral sensitizing dye moiety, thereby releasing a diffusible image dye. Such compounds are useful in radiation-sensitive elements and processes to provide dye images. Preferred compounds have the formula

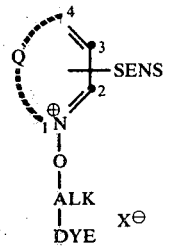

where:

Q represents the atoms to complete a pyridine or quinoline ring;

SENS is attached to the 2 or 4 position of the pyridine or quinoline ring and represents the atoms which, in conjunction with N, complete a spectral sensitizing dye;

ALK represents an alkylene moiety of 1 to 8 carbon atoms;

DYE represents a diffusible photographic dye or dye precursor moiety; and

X⊖ represents an anion, if necessary to provide charge neutrality.

3 Claims, No Sheets Drawing,

30 Pages Specification

The file of this unexamined application may be inspected and copies thereof may be purchased (849 O.G. 1221, Apr. 9, 1968).